US006992477B2

(12) United States Patent
Govari

(10) Patent No.: US 6,992,477 B2
(45) Date of Patent: Jan. 31, 2006

(54) MEDICAL DEVICE WITH POSITION SENSOR HAVING CORE WITH HIGH PERMEABILITY MATERIAL FOR DETERMINING LOCATION COORDINATES OF A PORTION OF THE MEDICAL DEVICE

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 135 days.

(21) Appl. No.: 09/882,125

(22) Filed: Jun. 15, 2001

(65) Prior Publication Data

US 2003/0006759 A1 Jan. 9, 2003

(51) Int. Cl.
*G01B 7/004* (2006.01)
*G01R 33/00* (2006.01)
*A61B 5/05* (2006.01)

(52) U.S. Cl. .......................... 324/207.13; 324/207.12; 324/207.15; 324/224; 600/424

(58) Field of Classification Search ........... 324/207.13, 324/207.22, 207.23, 207.24, 207.25, 207.26, 324/244, 260, 207.15, 224; 128/879; 600/424; 702/94, 150
See application file for complete search history.

(56) References Cited

U.S. PATENT DOCUMENTS

| 4,099,238 | A |   | 7/1978  | Suzuki |
|-----------|---|---|---------|--------|
| 4,247,601 | A | * | 1/1981  | Wiegand ..................... 428/611 |
| 4,327,416 | A |   | 4/1982  | Jerrim |
| 4,427,943 | A |   | 1/1984  | Cloutier et al. |
| 4,437,963 | A | * | 3/1984  | Yeoman ................... 204/228.3 |
| 4,538,082 | A |   | 8/1985  | Hinke et al. |
| 4,639,670 | A | * | 1/1987  | Normann ..................... 324/268 |
| 5,381,090 | A | * | 1/1995  | Adler et al. ................. 324/174 |
| 5,391,199 | A |   | 2/1995  | Ben-Haim |
| 5,443,489 | A |   | 8/1995  | Ben-Haim |
| 5,558,091 | A |   | 9/1996  | Acker et al. |
| 5,707,753 | A | * | 1/1998  | Kurihara et al. ............ 428/611 |
| 5,727,553 | A | * | 3/1998  | Saad .......................... 128/899 |
| 5,980,472 | A |   | 11/1999 | Seyl |
| 6,201,387 | B1|   | 3/2001  | Govari |
| 6,203,493 | B1|   | 3/2001  | Ben-Haim |
| 6,229,300 | B1|   | 5/2001  | Dlugos |

FOREIGN PATENT DOCUMENTS

| DE | 4224129 A    | 1/1994  |
| EP | 0 375 132 A1 | 6/1990  |
| EP | 1 055 392 A  | 11/2000 |
| EP | 02254181.5   | 5/2003  |

(Continued)

OTHER PUBLICATIONS

European Search Report, EP02254174, Sep. 25, 2002.

(Continued)

*Primary Examiner*—Jay Patidar
(74) *Attorney, Agent, or Firm*—Louis J. Capezzuto

(57) ABSTRACT

A medical location system includes a medical device having a body and a position sensor at a portion of the body. The position sensor has a core made of a Wiegand effect material and a winding circumferentially positioned around the core. The position sensor provides signals that are used to determine temperature at the position sensor and location information of the portion of the body of the medical device. A signal processor is coupled to receive the signals from the position sensor and the signal processor determines the temperature at the position sensor and location information of the portion of the body of the medical device based on the signals received from the position sensor.

44 Claims, 7 Drawing Sheets

FOREIGN PATENT DOCUMENTS

| GB | 1369902 A | 10/1974 |
| GB | 2 071 336 A | 9/1981 |
| WO | WO 94/04938 | 3/1994 |
| WO | WO 96/05768 | 2/1996 |
| WO | WO 97/24983 | 7/1997 |
| WO | WO 97/29682 A1 | 8/1997 |
| WO | WO 99/54685 A1 | 10/1999 |

OTHER PUBLICATIONS

H.J. Gevatter et al., "Wiegand Effect Position and Speed Sensors", Technisches Messen TM, R. Oldenbourg Verlag, Munchen, Germany, vol. 51, No. 4, Apr. 1984, pp. 123-129, XP002027038, p. 126, left-hand column, paragraph 3.1, Figure 8 (English Abstract on first page or article).

European Search Report, dated Oct. 17, 2002, for European Appln. No. EP 02 25 4182.

European Search Report EP 02254181 dated Nov. 12, 2003.

Dlugos, D. J.: "Wiegand Effect Sensors Theory and Applications", Sensors Magazine, May 1998. Available online at http://www.sensormag.com/articles.

* cited by examiner

REGRESSING HEAT EXPERIMENT

| | 1 | | | 2 | | | 3 | | | 4 | |
|---|---|---|---|---|---|---|---|---|---|---|---|
| | sensitivity | | resistance | sensitivity | | resistance | sensitivity | | resistance | sensitivity | | resistance |
| 30 | 2.6290 | 1.39 | 176.30 | 12.59 | 2.3925 | 1.30 | 165.20 | 12.89 | 2.4537 | 1.31 | 171.80 | 13.17 | 2.6864 | 1.26 | 185.60 | 13.25 |
| 35 | 2.6327 | 1.25 | 178.90 | 10.96 | 2.3958 | 1.18 | 168.00 | 11.01 | 2.4567 | 1.18 | 174.30 | 11.42 | 2.6896 | 1.14 | 188.90 | 11.28 |
| 40 | 2.6356 | 1.13 | 181.80 | 9.19 | 2.3990 | 1.03 | 171.00 | 9.06 | 2.4598 | 1.06 | 177.20 | 9.50 | 2.8728 | 1.03 | 192.10 | 9.42 |
| 45 | 2.6390 | 1.00 | 184.40 | 7.65 | 2.4025 | 0.86 | 173.90 | 7.25 | 2.4632 | 0.92 | 179.90 | 7.95 | 2.8765 | 0.90 | 194.90 | 7.85 |
| 50 | 2.6419 | 0.89 | 187.40 | 5.92 | 2.4057 | 0.74 | 176.40 | 5.73 | 2.4670 | 0.76 | 182.80 | 6.95 | 2.8801 | 0.77 | 197.80 | 6.27 |
| 55 | 2.6457 | 0.75 | 190.40 | 4.25 | 2.4087 | 0.62 | 178.90 | 4.25 | 2.4705 | 0.62 | 185.30 | 4.80 | 2.8838 | 0.64 | 200.80 | 4.58 |
| 60 | 2.6489 | 0.63 | 192.80 | 2.96 | 2.4116 | 0.50 | 181.80 | 2.59 | 2.4744 | 0.45 | 188.20 | 3.19 | 2.8875 | 0.52 | 203.80 | 3.14 |
| 65 | 2.6519 | 0.51 | 195.80 | 1.38 | 2.4148 | 0.36 | 184.30 | 1.19 | 2.4774 | 0.34 | 191.80 | 1.25 | 2.8913 | 0.38 | 207.30 | 1.40 |
| 70 | 2.6567 | 0.37 | 198.50 | 0.00 | 2.4176 | 0.25 | 186.50 | 0.00 | 2.4799 | 0.24 | 194.20 | 0.00 | 2.8952 | 0.25 | 210.20 | 0.00 |
| 75 | 2.6599 | 0.21 | | | 2.4207 | 0.12 | | | 2.4833 | 0.10 | 196.40 | | 2.8986 | 0.13 | 212.20 | |
| 80 | 2.6555 | 0.00 | | | 2.4236 | 0.00 | | | 2.4859 | 0.00 | | | 2.9024 | 0.00 | | |
| slope | −0.0266 | | −0.3165 | | −0.0250 | | −0.3233 | | −0.0289 | | −0.3305 | | −0.0254 | | −0.3279 | |

| | 5 | | | 6 | | | 7 | | | 8 | |
|---|---|---|---|---|---|---|---|---|---|---|---|
| | sensitivity | | resistance | sensitivity | | resistance | sensitivity | | resistance | sensitivity | | resistance |
| 30 | 3.3480 | 1.00 | 235.7 | 12.16 | 2.4057 | 1.25 | 167.4 | 13.02 | 2.4290 | 1.32 | 160.32 | 20.27 | 2.5002 | 1.11 | 175.40 | 11.74 |
| 35 | 3.3506 | 0.92 | 239.3 | 10.49 | 2.4061 | 1.15 | 169.6 | 11.56 | 2.4319 | 1.20 | 161.70 | 19.23 | 2.5029 | 1.00 | 177.40 | 10.48 |
| 40 | 3.3533 | 0.84 | 242.8 | 8.90 | 2.4108 | 1.04 | 171.9 | 10.06 | 2.4356 | 1.05 | 166.30 | 15.94 | 2.5053 | 0.91 | 179.20 | 9.38 |
| 45 | 3.3568 | 0.74 | 246.7 | 7.17 | 2.4141 | 0.90 | 174.7 | 8.30 | 2.4387 | 0.92 | 171.00 | 12.75 | 2.5070 | 0.84 | 180.60 | 8.53 |
| 50 | 3.3605 | 0.62 | 250.9 | 5.38 | 2.4157 | 0.79 | 177.3 | 6.71 | 2.4428 | 0.75 | 172.90 | 11.51 | 2.5093 | 0.75 | 183.50 | 6.81 |
| 55 | 3.3642 | 0.51 | 254.4 | 3.93 | 2.4196 | 0.66 | 179.6 | 5.35 | 2.4452 | 0.61 | 174.10 | 10.74 | 2.5134 | 0.58 | 185.10 | 5.89 |
| 60 | 3.3674 | 0.42 | 258.7 | 2.20 | 2.4232 | 0.52 | 182.2 | 3.84 | 2.4494 | 0.48 | 183.90 | 4.84 | 2.5157 | 0.49 | 191.40 | 2.40 |
| 65 | 3.3708 | 0.32 | 261.7 | 1.03 | 2.4265 | 0.38 | 184.6 | 2.49 | 2.4516 | 0.39 | 190.20 | 1.37 | 2.5168 | 0.45 | 194.10 | 0.98 |
| 70 | 3.3749 | 0.20 | 264.4 | 0.00 | 2.4293 | 0.27 | 186.9 | 1.23 | 2.4546 | 0.25 | 192.80 | 0.00 | 2.5215 | 0.26 | 196.00 | 0.00 |
| 75 | 3.3780 | 0.10 | 267.9 | | 2.4326 | 0.13 | 189.2 | 0.00 | 2.4580 | 0.13 | | | 2.5247 | 0.13 | | |
| 80 | 3.3815 | 0.00 | | | 2.4358 | 0.00 | | | 2.4511 | 0.00 | | | 2.5280 | 0.00 | | |
| slope | −0.205 | | −0.3124 | | −0.0253 | | −0.2934 | | −0.0266 | | −0.5271 | | −0.0219 | | −0.3069 | |

FIG. 6

MEDICAL DEVICE WITH POSITION SENSOR HAVING CORE WITH HIGH PERMEABILITY MATERIAL FOR DETERMINING LOCATION COORDINATES OF A PORTION OF THE MEDICAL DEVICE

FIELD OF THE INVENTION

The present invention relates generally to object tracking systems, and specifically to position sensors having high sensitivity at high temperatures for tracking the position and orientation of a medical device.

BACKGROUND OF THE INVENTION

In many medical procedures, devices, such as probes, endoscopes, catheters, stents and tags/markers are inserted into a patient's body. Such devices are used for a large variety of procedures including irreversible surgical actions, such as ablation and taking of tissue samples. Therefore, it is necessary to have accurate information on the position and orientation of the probe within the patient's body.

Electromagnetic position determining systems provide a convenient method of receiving accurate information on the position and orientation of intra-body objects, and allow accurate tracking of these objects. Such systems are described for example in U.S. Pat. Nos. 5,558,091, 5,391,199 and 5,443,489, and in International Patent Publications WO94/04938 and WO96/05768, whose disclosures are incorporated herein by reference. These systems determine the coordinates of a device using one or more field sensors, such as a Hall effect device, coils or other antennas carried on the device. The field sensors are transducers used as position sensors and are typically located at or adjacent the distal end of the device, and/or along the length of the device. Therefore, the transducers are preferably made as small as possible so as to fit into the device without interfering with the device's maneuverability or increasing its size unduly.

U.S. Pat. No. 5,558,091 describes a Hall effect sensor assembly of a cube shape which includes three mutually orthogonal, thin galvanomagnetic films. This sensor assembly is preferably of dimensions about 3×0.75×0.75 mm. The U.S. Pat. No. 5,558,091 further describes another Hall effect sensor assembly which includes three field sensing elements in the form of semiconductor chips. Each chip includes one or more elongated bars of a magnetoresistive material. Each such chip is sensitive to magnetic field components in the direction of the bar. This assembly preferably has a diameter of 0.8 mm or less. However, such chips suffer from nonlinearities, saturation effects, hysteresis and temperature drifts.

Therefore, most magnetic position determining systems use sensors formed of miniature coils that include a large number of turns of an electrically conducting wire. Such coils are described, for example, in PCT publications PCT/GB93/01736, WO94/04938 and WO96/05768, in the above mentioned U.S. Pat. No. 5,391,199, and in PCT publication PCT/IL97/00009, which is assigned to the assignee of the present application, all of which are incorporated herein by reference. The performance of a sensor coil is dependent on its inductance, which is a function of the number of turns of the coil times the cross sectional area of the coil. Therefore, in planning and designing a miniature coil for use within a surgical device, for example, it is generally necessary to make a compromise between performance and the size of the coil. Such coils are typically used in position sensors having three mutually orthogonal sensor coils and typically have minimum dimensions of 0.6×0.6×0.6 mm and more generally of 0.8×0.8×0.8 mm. It has always been believed that smaller coils of the same type would not provide acceptable performance and are also hard to manufacture. Additionally, given these fixed size limitations, no sensor coils have been developed that have an outer diameter less than 0.6 mm.

Moreover, for these types of position sensors, it is common for the sensor coil to include a core. For those position sensors (sensor coil) that utilize a core, it is known that the material for the core can consist of two acceptable materials. The first material is ferrite and has been used with success as a core material for medical devices having a sensor coil with a core.

The later core material developed that has also proved to be effective as core material for a sensor coil in a medical device is carbonyl iron. However, for both types of core materials, the sensor coils utilizing such core material would be generally limited to the outer diameter minimum dimension requirements described above.

In order to determine both translational and rotational coordinates, some position determining systems, such as the system described in the above-mentioned PCT publication WO96/05768, use three sensor coils, having respective axes that are mutually linearly independent, preferably mutually orthogonal. Preferably, these three coils are packaged together to form a sensor assembly, which is used to provide six-dimensional position and orientation coordinate readings. The use of an assembly which has the three coils within one package allows easy insertion and/or attachment of the coils to devices such as catheters. Also, the assembly provides exact positioning of the coils relative to each other, thus simplifying the calibration of position determining systems using the coils. Generally, the coils are enclosed in a cylindrical-shaped case, which protects the coils from the surroundings.

In the system of the '768 publication, this assembly typically has a length of about 6 mm and a diameter of about 1.3 mm. Because the axes of the coils need to be generally mutually orthogonal in order to achieve accurate position sensing in all six dimensions, it is not possible to make the diameter of the assembly much smaller.

Although this coil assembly fits into most medical devices, in some cases coils of equivalent performance and smaller width are desired. For example, U.S. Pat. No. 6,203,493, which is assigned to the assignee of the present invention and is incorporated herein by reference, describes a method of enhancing the accuracy of position determination of an endoscope that includes miniature position sensing coils, by distancing the coils from metallic apparatus within the endoscope. If the coil assembly can be made with a smaller width, it is then possible to increase the separation between the miniature coils and the metallic apparatus, and thus achieve better accuracy from the position determining system.

Coils made by photolithography or VLSI procedures are known as disclosed in U.S. Pat. No. 6,201,387 B1, which disclosure is incorporated herein by reference, in which these coils are referred to as photolithographic coils. Photolithographic coils are generally made in the form of a spiral conductor printed on a substrate of plastic, ceramic or semiconductor material. Such coils conventionally comprise up to four overlapping spiral layers, using currently available fabrication techniques.

Photolithographic coils or antennas are also commonly used in contactless smart cards, as are known in the art. These cards inductively communicate with and receive power from a reader circuit through a photolithographic coil or antenna embedded in the card. Because smart cards are limited in thickness to less than 0.8 mm, they generally include only a single coil, whose axis is necessarily perpendicular to the plane of the card. To communicate with the reader, the smart card must be properly oriented, so that the coil axis is aligned with a magnetic field generated by the reader, in order to achieve proper coupling.

Reducing the width or outer diameter of the coil assembly would allow position determining systems to be used with narrower devices, which generally have superior maneuverability and ease of access to remote locations. Alternatively, reducing the width or outer diameter of the coil assembly would allow the assembly to occupy a smaller portion of the cross-sectional area of the device, leaving more space for functional apparatus and/or working channels along the devices.

To date, there have been no position sensors or sensor coils having outer diameters that are smaller in size than the sensors described above and are capable of achieving performance measures such as maintaining a high degree of accuracy at high temperatures.

SUMMARY OF THE INVENTION

The present invention is directed toward a position sensor for a medical device comprising a core made of a Wiegand effect material and a winding circumferentially positioned around the core. The position sensor is used to determine position and/or orientation coordinates.

The position sensor maintains accuracy within $\leq 1$ mm at temperatures greater than 75° C. Moreover, the position sensor preferably maintains accuracy within <1 mm at temperatures at approximately 80° C.

The core of the position sensor according to the present invention has an outer diameter of less than approximately 0.3 mm and preferably the core has an outer diameter of about 0.25 mm. Additionally, in one embodiment, the winding is attached to the core. Moreover, a combination of the core and the winding have an outer diameter of less than approximately 0.5 mm and preferably an outer diameter of about 0.4 mm.

The core of the position sensor for one embodiment in accordance with the present invention comprises cobalt, vanadium and iron. Moreover, the material of the core comprises approximately 20–80% cobalt in one embodiment. In another embodiment according to the present invention, the material of the core comprises approximately 2–20% vanadium. In another embodiment of the present invention, the material of the core comprises approximately 25–50% iron. In a preferred embodiment according to the present invention, the material of the core comprises approximately 52% cobalt, 10% vanadium and 38% iron.

In a preferred embodiment of the present invention, the position sensor has accuracy to within approximately 0.5 mm. This type of accuracy is achieved with the position sensor in accordance with the present invention through the use of a position sensor having a core made of a high permeable material wherein the material is a magnetic material that produces a magnetic field that switches polarity and causes a substantially uniform voltage pulse upon an application of an external field.

In an alternative embodiment of the position sensor according to the present invention, the material of the core comprises a copper, nickel, and iron alloy (CuNiFe). In another embodiment of the position sensor according to the present invention, the material of the core comprises an iron, chrome, and cobalt alloy. These alternative embodiments for the core material also ensure accuracy within approximately 0.5 mm for the position sensor according to the present invention.

The present invention further includes a medical device and position sensor combination comprising a medical device having a body and a position sensor attached to the body wherein the position sensor has a core made of Wiegand effect material and a winding circumferentially positioned around the core. The various embodiments for the position sensor outlined above are used in the medical device and position sensor combination in accordance with the present invention.

Both the position sensor and the medical device and position sensor combination, both in accordance with the present invention, are used in conjunction with a position and orientation system that maintains accuracy even at high temperatures.

The present invention also includes a method for measuring temperature at a site within a patient during a medical procedure. The method in accordance with the present invention comprises providing a medical device having a position sensor and placing the medical device within the patient and positioning the position sensor at the site. A temperature measurement signal is provided to the position sensor and voltage is measured at the position sensor. A resistance value is determined based on the temperature measurement signal and the voltage and a temperature value based on the resistance value is then determined. The method for measuring temperature in accordance with the present invention utilizes the various embodiments for the position sensor and medical device and position sensor combination as outlined above.

An algorithm stored in the memory of a signal processor utilized by the position and orientation system is used to determine the temperature at or adjacent the position sensor of the medical device. The algorithm further includes utilizing a resistance drift factor which is added to the measured resistance value in accordance with the algorithm according to the present invention.

The temperature measurement method in accordance with the present invention further comprises generating an externally applied field such as an AC magnetic field at the site within the patient. The externally applied field is caused by a generator signal provided to a plurality of magnetic field generators. The temperature measurement signal is at a different frequency than the generator signal.

In one embodiment, the temperature measurement signal is at 4 KHz and the generator signal is at 3 KHz.

The present invention further includes a method for adjusting for temperature sensitivity of a medical device having a position sensor wherein the method comprises the steps of providing a medical device having a position sensor and measuring voltage at the position sensor. A resistance value is determined from the measured voltage and a temperature value is determined at the position sensor based on the resistance value. Additionally, a sensitivity is determined at the position sensor based on the temperature and location information provided by the position sensor is adjusted based on the sensitivity.

The method for adjusting for temperature sensitivity in accordance with the present invention utilizes the position sensor and medical device having position sensor combination as outlined above.

In accordance with the present invention, the location information derived from the position sensor is in the form of position and/or orientation coordinates. In accordance with the present invention, a sensitivity algorithm is stored in the memory of the signal processor of the position and orientation system. The temperature sensitivity algorithm applies a resistance drift factor to the resistance value determined by the method for adjusting for temperature sensitivity of the medical device having the position sensor in accordance with the present invention.

Additionally, the sensitivity of the position sensor is determined by applying a sensitivity drift factor to the temperature value determined above. The sensitivity drift factor is stored in the memory of a signal processor. Both the resistance drift factor and the sensitivity drift factor are derived from a resistance versus temperature profile of the position sensor and a sensitivity versus temperature profile of the position sensor respectively. Both the resistance versus temperature profile of the position sensor and the sensitivity versus temperature profile of the position sensor are prestored in the memory of the signal processor of the position and orientation system in accordance with the present invention.

These and other objects, features and advantages of the present invention will be more readily apparent from the detailed description set forth below, taken in conjunction with the accompanying drawings.

BRIEF DESCRIPTION OF THE DRAWINGS

FIG. 6 is a Table illustrating numerous data from a regressing heat experiment.

DESCRIPTION OF THE PREFERRED EMBODIMENTS

For purposes of this disclosure, the terms "sensor coil", "coil", "position sensor" and "location sensor" have the same meaning and are used interchangeably. A position sensor is a sensor that provides location information in the form of signals that determine position and/or orientation coordinates of the position sensor in the manner described above.

Figure 1A:
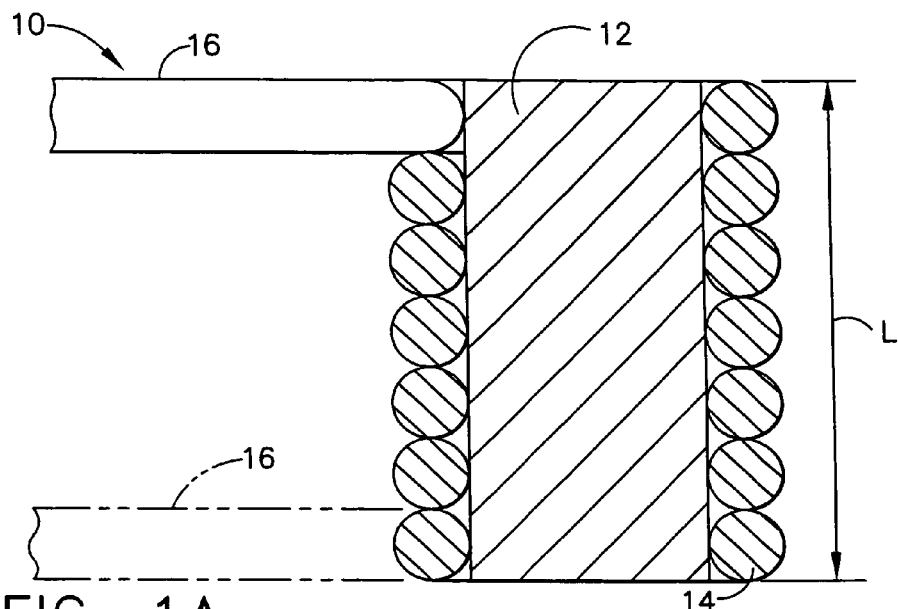
FIG. 1A is a view in cross-section of a sensor coil having a core for use as a position sensor in accordance with the present invention.
Figure 1B:
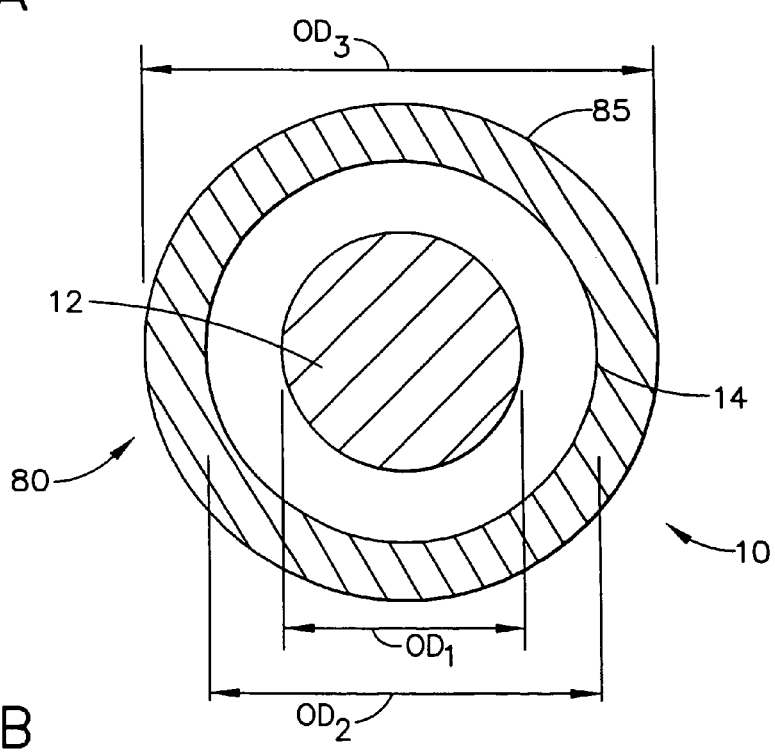
FIG. 1B is a view in cross-section of the sensor coil of FIG. 1A as a position sensor attached to a body of a medical device.

The present invention, as best illustrated in FIGS. 1A and 1B, show a position sensor according to the present invention comprising a sensor coil 10 having a core 12 made of Wiegand effect material, which is described in greater detail below, and a winding (in the form of copper wire) attached to or circumferentially wrapped around the core 12. The sensor coil 10 is particularly useful as a position sensor for a medical device 80 as shown in FIG. 1B. As mentioned previously, the sensor coil 10 is used as a position sensor for determining location information in the form of position coordinate and/or orientation coordinates.

The sensor coil 10 preferably has a length L of approximately 3.0–4.0 mm although the length L can be longer. Wires 16 are connected to the sensor coil 10 leading from the winding wire 14 wherein the wires 16 are operatively connected to a circuit for measurement of the voltage induced in the sensor coil 10.

As shown in FIG. 1B, the core 12 of the sensor coil 10 has an outer diameter ($OD_1$) less than 0.3 mm and preferably an $OD_1$ of about 0.25 mm. The total outer diameter for the sensor coil 10 ($OD_2$) is less than 0.5 mm and preferably an $OD_2$ of about 0.4 mm. Due to the extremely compact size of the sensor coil 10 according to the present invention, the sensor coil 10 can be accommodated in the body 85 of the medical device 80 wherein the medical device 80 has an outer diameter ($OD_3$) less than or equal to approximately 0.67 mm (2F or less). Thus, sensor coil 10 is useful as a position sensor in various medical devices 80. For instance, the medical device 80 preferably includes devices such as a catheter, a probe, a stent, a tag or marker, etc. At these dimensions, the medical device 80 including the sensor coil 10 according to the present invention is utilized in various medical applications such as diagnostic and/or therapeutic procedures performed in the various tissue and organs of a patient's body.

The sensor coil 10 according to the present invention is particularly useful for medical devices 80 using a single sensor coil as a position sensor although it can be utilized in position sensors having multiple sensor coil arrangements such as three mutually orthogonal sensor coils. Medical devices 80 using an arrangement of only one sensor coil 10 are referred to as a "single axis system". For the sensor coil 10 according to the present invention, the sensor coil 10 has a length L that is at least two to three times the outer diameter $OD_2$ of the sensor coil 10 and preferably a length L that is greater than six times the $OD_2$ of the sensor coil 10. Thus, the sensor coil 10 according to the present invention is more sensitive than the prior art sensor coils having ferrite or carbonyl iron cores. Moreover, the length/OD ratio of the sensor coil 10 ensures that the sensor coil 10 is easier and cheaper to manufacture since it is mechanically more stable in comparison with sensor coils having ferrite material with a similar length/OD ratio which would tend to result in a sensor core that is brittle.

Core Material

In accordance with the present invention, the material for the core 12 is a material of high permeability and high mechanical flexibility such as Wiegand effect material, which may be in the form of a wire. Wiegand effect material is usually produced by cold working a 0.010 inch diameter ferromagnetic wire. The wire is made from Vicalloy which is a mixture of cobalt, iron, and vanadium (manufactured by HID Corporation of North Haven, Conn., USA). This material is a specially work hardened, self-nucleating bi-stable magnetic material, which can be in the form of a wire, and can generate pulses up to 600 millivolts without any electrical inputs. It works by control of the Barkhausen jumps. For purposes of this disclosure, the terms "Wiegand effect material", "Wiegand material, "Wiegand alloy", and "Wiegand wire" have the same meaning and are used interchangeably.

With respect to the use of this Wiegand effect material for the core 12 of the sensor coil 10, the material comprises various mixture combinations of cobalt, vanadium and iron respectively. For instance, in one embodiment for the sensor coil 10, the core material comprises approximately 20%–80% cobalt and the remaining percentage of the material comprises vanadium and iron. In another embodiment for the sensor coil 10, the core material comprises approximately between 2%–20% vanadium and the remaining percentage of the material comprises cobalt and iron. In another embodiment of the sensor coil 10, the core material comprises approximately between 25%–50% iron and the remaining percent of the material comprises cobalt and vanadium.

In a preferred embodiment for the core 12 of the sensor coil 10, the core material comprises approximately 52% cobalt, 10% vanadium and 38% iron. It is important to note that core material for the core 12 may comprise any desired combination and percentage of composition in addition to those combinations illustrated above.

The cold working process utilized on the Wiegand effect material consists of several steps of increasing amounts of twist and detwist of the Wiegand material (wire) under applied tension.

The Wiegand effect wire is then age hardened to hold in the tension built up during the cold working process. This process causes the Wiegand effect material to have a soft magnetic center and a work hardened surface, which has a higher magnetic coercivity, called the "shell".

When an alternating magnetic field of proper strength is applied to the Wiegand material, the magnetic field of the material center switches polarity and then reverses, causing a sharp, substantially uniform voltage pulse to be generated wherein the pulse is commonly referred to as a "Wiegand Pulse". The cold working process to produce Wiegand material permanently "locks" the ability to exhibit the well known Barkhausen jump discontinuities into the material.

Figure 5:
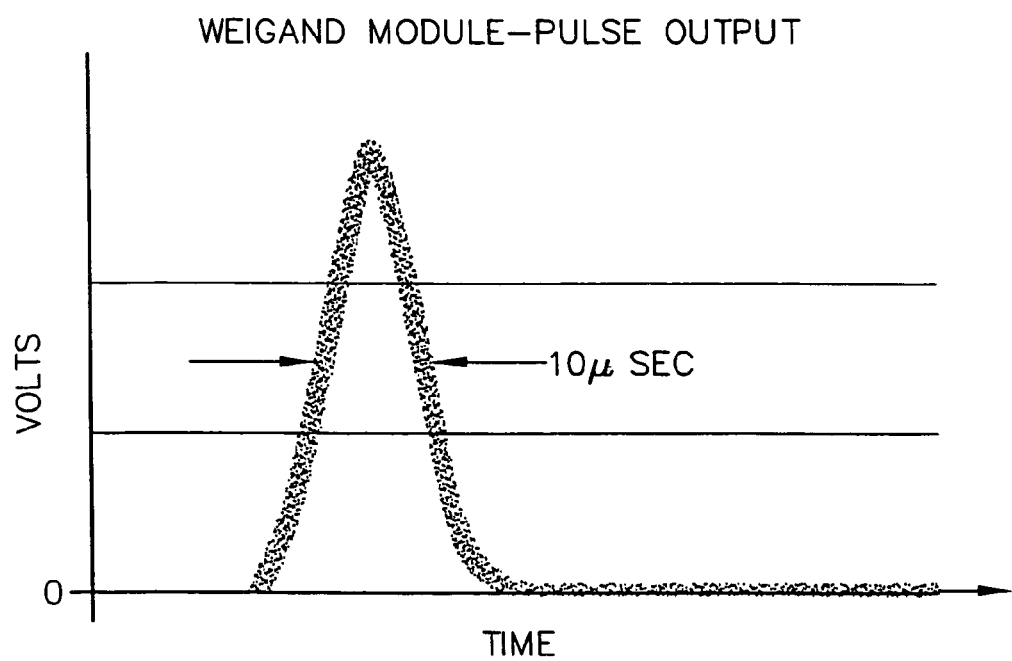
FIG. 5 is a graph of the pulse output for the Wiegand effect material of the position sensor according to the present invention plotting voltage as a function of time.

With the Wiegand effect material as a core material, magnetic switching occurs when the Wiegand material is in the presence of alternating longitudinal magnetic fields. Since the resultant hysteresis loop contains large discontinuous jumps known as Barkhausen discontinuities which occur due to shell and center polarity switching. The magnetic switching action of the Wiegand material induces a voltage across the pick-up coil windings 14 of approximately 10 microseconds in duration as shown in FIG. 5.

With the Wiegand material, the pulse amplitude is not totally dependent on excitation field strength and orientation. The alternating positive and negative magnetic fields of equal saturating strength are used to magnetize and trigger the Wiegand material when in use for the position sensor 10. These alternating magnetic fields are produced by an alternating current generated field.

Moreover, the Wiegand effect is operational at temperatures ranging between −80° C. to 260° C. Thus, functional temperature range of each position sensor 10 is based on the limitations of various component subparts of the individual sensor.

Additionally, in an alternative embodiment of the present invention, the core 12 of the sensor coil 10 consists of an alloy material comprising a mixture of copper, nickel and iron (CuNiFe). Alternatively, another embodiment of the present invention uses a core 12 consisting of an alloy material comprising a mixture of iron, chrome and cobalt, for instance, ARNOKROME™ manufactured by the Rolled Products Division of the Arnold Engineering Company (SPC Technologies, Marengo, Ill., USA). Both of these materials, e.g. CuNiFe and iron, chrome and cobalt alloys are also highly permeable and highly mechanically flexible materials and are utilized as core material 12 for the sensor coil 10 in accordance with the present invention.

Temperature Sensitivity Testing

In accordance with the present invention, temperature sensitivity testing was conducted on the position sensor 10 for the development of a temperature sensitivity algorithm (described in detail below) particular to a location system 30 (FIG. 4) having one sensor coil 10 as the position sensor on the medical device 80, particularly, the single axis system described in commonly assigned U.S. patent application Ser. No. 09/620,316, filed on Jul. 20, 2000 which disclosure is incorporated herein by reference. Accordingly, the temperature sensitivity algorithm is used in conjunction with the position and orientation algorithm of the location system 30 (FIG. 4), for instance a single axis location system, in order to compensate for changes in temperature sensitivity for utilizing the position sensor 10 at high temperatures while maintaining a high degree of accuracy, for instance, $\leq 1$ mm and preferably $\leq 0.5$ mm in accordance with the present invention.

Figure 3A:
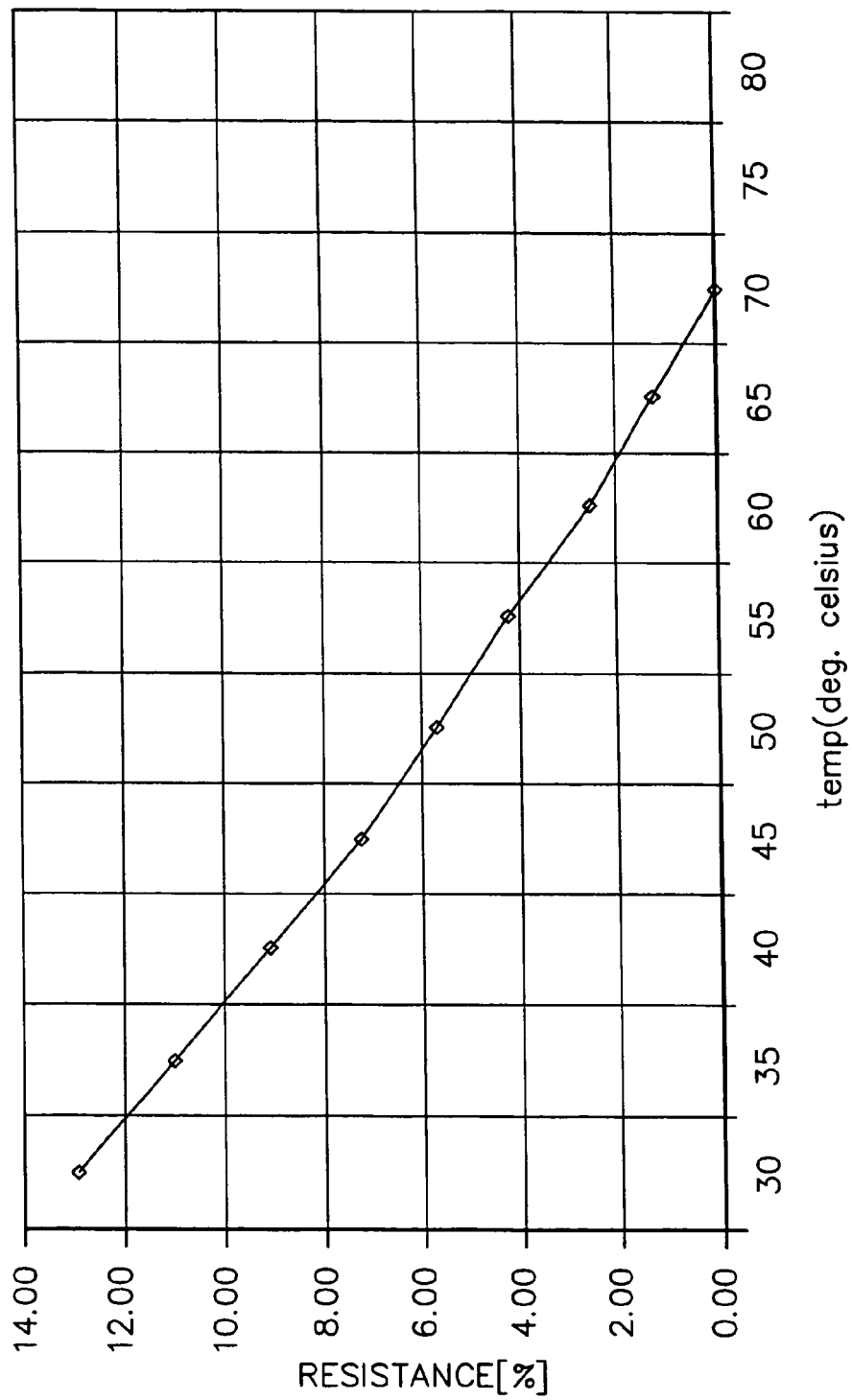
FIG. 3A is a chart indicating a regressing heat experiment for the position sensor according to the present invention plotting resistance as a function of temperature.
Figure 3B:
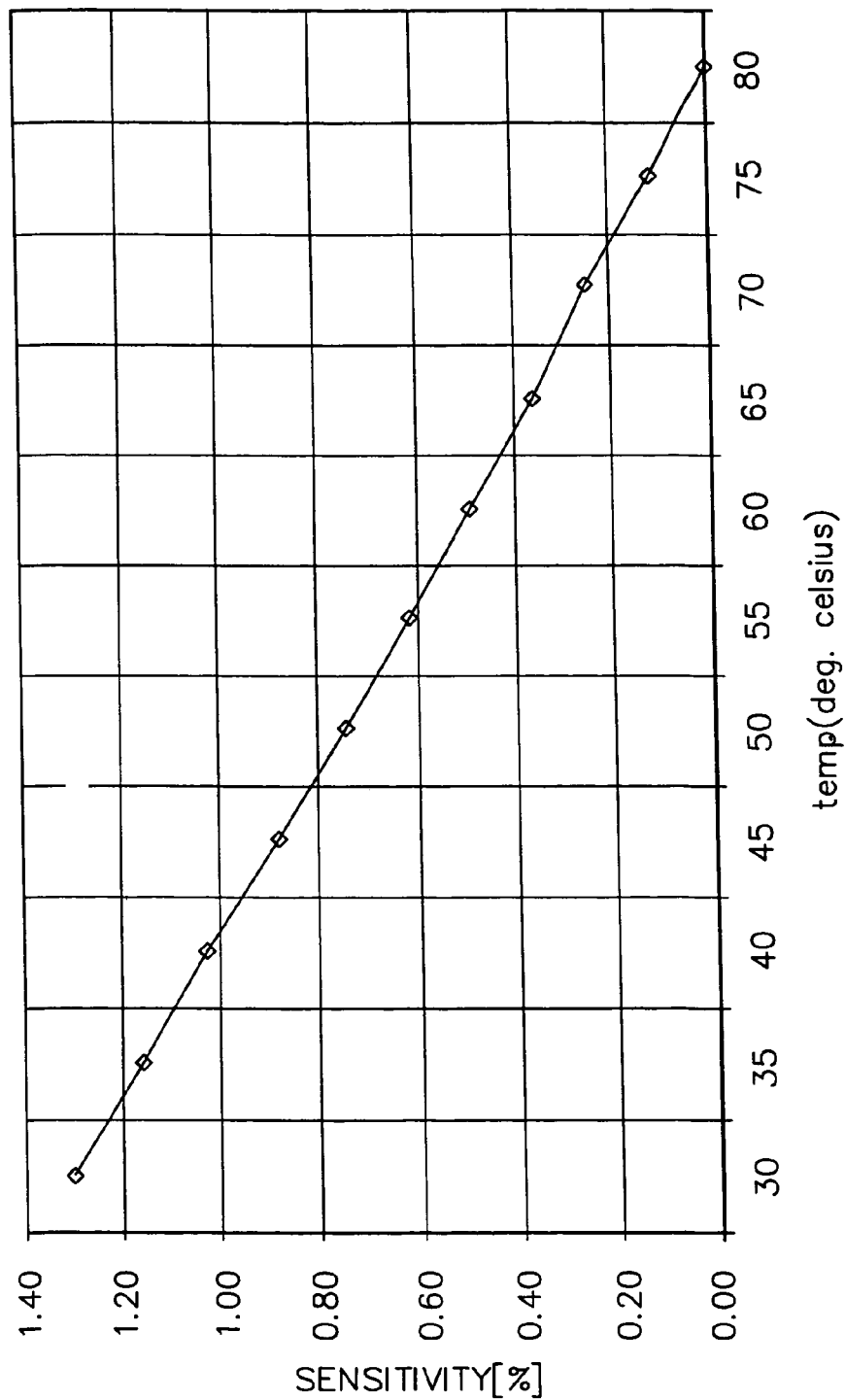
FIG. 3B is a chart reflecting a regressing heat experiment for the position sensor according to the present invention plotting sensitivity as a function of temperature.

In creating the temperature sensitivity algorithm according to the present invention, heat regression tests were conducted in order to test the resistance and sensitivity for the sensor coils 10 having cores 12 made of Wiegand effect material as a function of temperature as best shown in Table (FIG. 6) and FIGS. 3A and 3B. These tests established values and ranges particular to the position sensor 10 of the present invention. For instance, these predetermined values include a resistance drift value ($G_r$) over a large temperature range (30° to 80° C.) for the sensor resistance versus temperature results shown in FIG. 3A and Table (FIG. 6) and a sensitivity drift value ($G_s$) over the same 30° to 80° C. temperature range for the sensor sensitivity versus temperature results shown in FIG. 3B and Table (FIG. 6).

Figure 2:
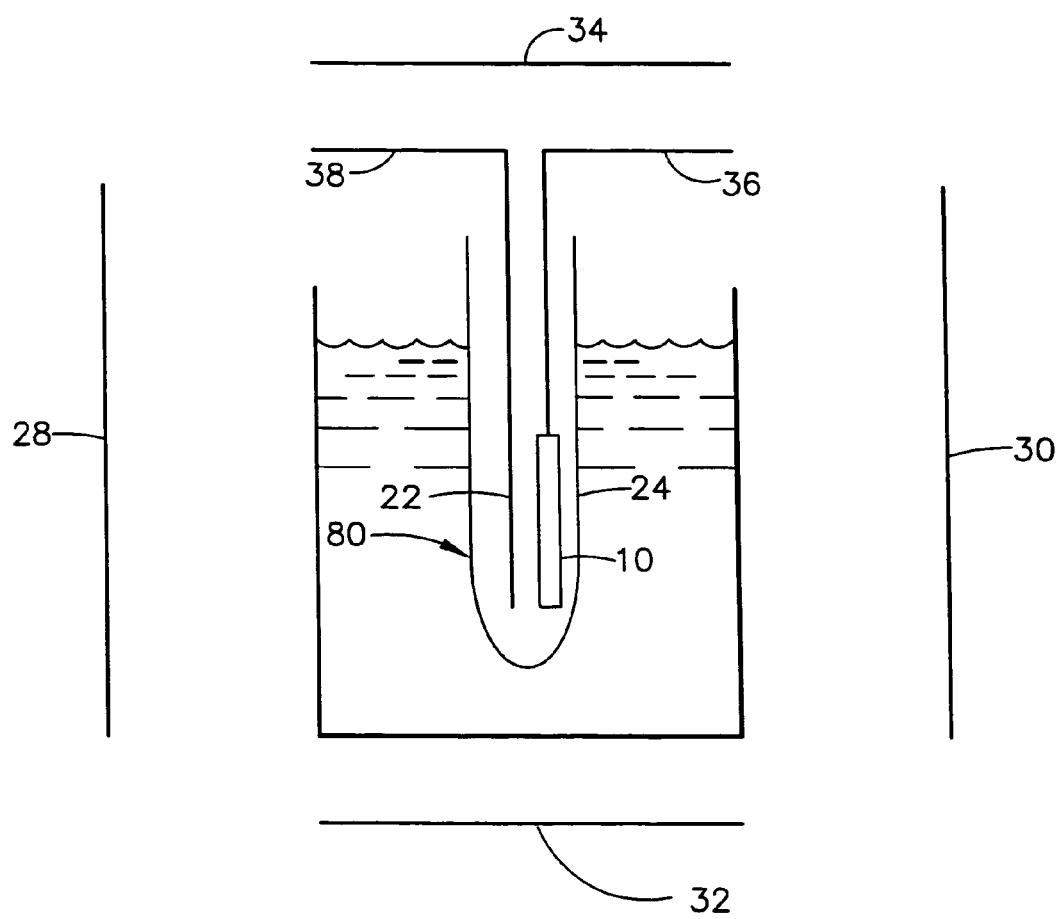
FIG. 2 is a schematic illustration of a testing apparatus for the position sensor and medical device of FIGS. 1A and 1B according to the present invention.

These values were predetermined by testing the effect of the sensor core 12 composition (Wiegand effect material) on the temperature sensitivity for twenty sensors 10 (data from eight position sensors 10 representative of all twenty sensors 10 tested are listed in Table of FIG. 6). For this test, each location sensor 10 consisted of a single sensor coil 10 having core 12 made of Wiegand effect material. The temperature sensitivity for each of the sensor coils 10, as the position sensor, were tested in an apparatus as schematically shown in FIG. 2. Accordingly, position sensor (sensor coil 10) and thermocouple 22 were inserted into a glass tube 24, which was, in turn, placed in a hot water bath 26. Each sensor coil 10 and thermocouple 22 have wire leads 36 and 38, respectively which are attached to instruments to measure sensor voltage and temperature, respectively. Water was poured into the bath to a level sufficient to submerge each sensor 10. The bath was placed inside a Helmholtz chamber, consisting of three pairs of mutually orthogonal Helmholtz coils.

FIG. 2 shows two of the three pairs of Helmholtz coils; the first pair consisting of Helmholtz coils 28 and 30; and the second pair consisting of Helmholtz coils 32 and 34. The Helmholtz coils are arranged such that the distance between the Helmholtz coils in a pair is equal to the radius of each of the Helmholtz coils in the pair. In the Helmholtz chamber, each pair of Helmholtz coils is disposed coaxially, the three pairs of Helmholtz coils having three, mutually orthogonal axes. The Helmholtz chamber has the property that the magnetic field within the chamber is relatively invariant with distance from the center of the chamber. Nevertheless, in testing the position sensors 10, efforts were made to locate the sensors 10 in the same spot within the chamber. The Helmholtz coils were energized with alternating current (AC) having a frequency of 3 KHz. Sensor voltages were measured from one sensor coil 10 in each position sensor in five degree increments over the temperature range of 30° to 80° C. Measurements were performed on the twenty position sensors 10 wherein the sensor coil cores 12 were all made of Wiegand effect material for determining parameters such as resistance drift $G_r$, temperature sensitivity drift $G_s$, resistance drift versus temperature slope $a_0$ and sensitivity drift versus temperature slope $b_0$ used to establish a sensitivity correction S(T), e.g. as part of a real time sensitivity compensation algorithm for the position and orientation algorithm of the location system 30.

A 4 KHz signal is sent through the sensor coil 10 and the voltage across the coil 10 is measured. The ratio of voltage and the 4 KHz current (I) is the resistance. The 4 KHz signal is used in order not to disturb the other frequencies of the system 30 which are below 4 KHz.

Figure 4:
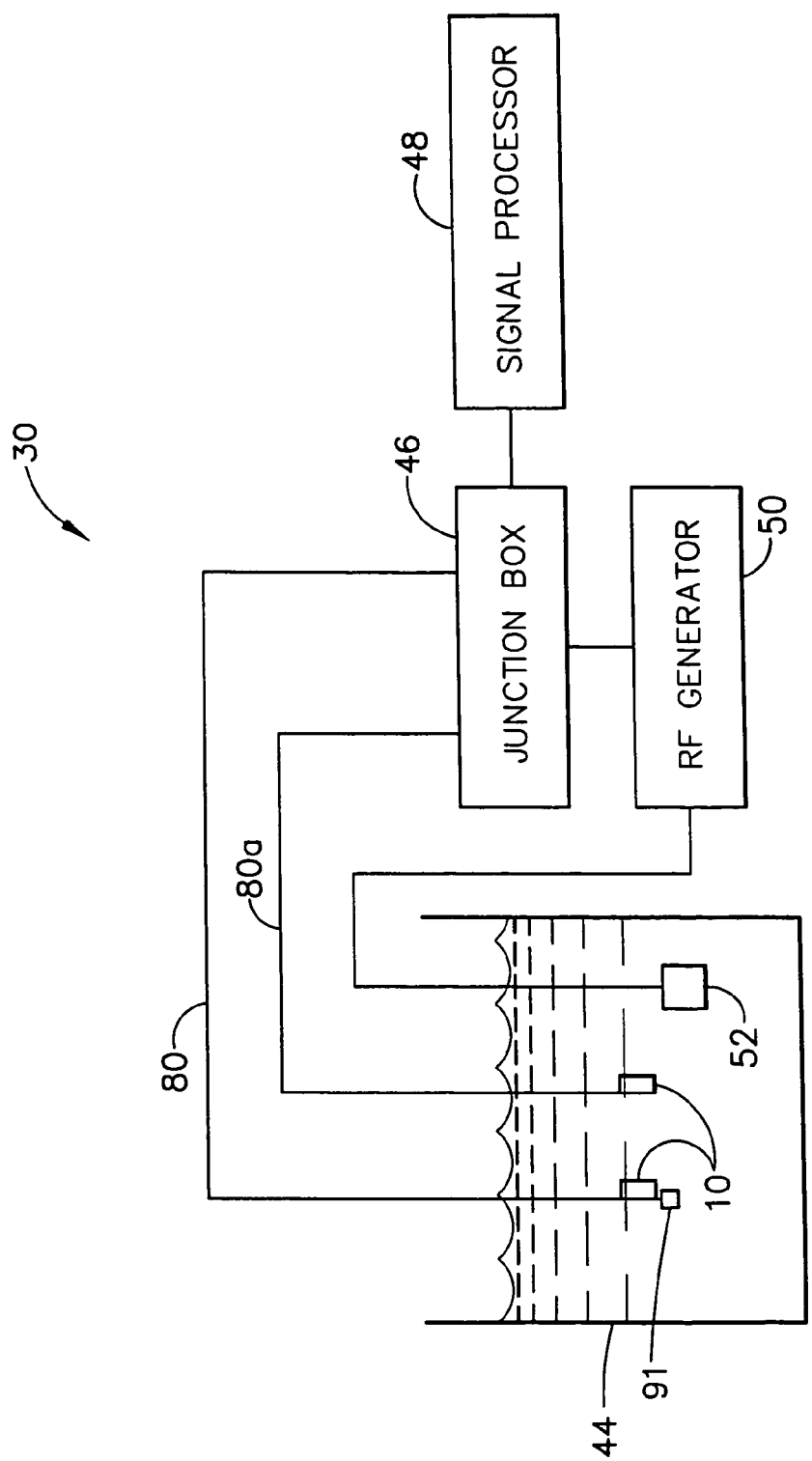
FIG. 4 is a schematic illustration of another test system utilizing the position sensor according to the present invention.

First, since the current (I) delivered through each sensor 10 is consistent and uniform (from a 4 KHz signal delivered by the position and orientation system 30 shown in FIG. 4), the voltages read on each sensor 10 at each temperature were converted to a resistance value by signal processor 48.

Resistance drift values $G_r$ were plotted against temperature as illustrated in FIG. 3A and Table (FIG. 6). The resistance values (in ohms) were measured at each temperature along the selected temperature range (30° to 80° C.) and were converted to the gradient values $G_r$ (as % drift of resistance), i.e. the percentage difference of a sensor coil resistance at temperature T relative to its resistance at 80° C. according to the equation:

$$Gr\ (\%) = \frac{|R(T) - R(80)|}{R(80)} \times 100$$

wherein $G_r$ is resistance drift as the gradient value in percent (% drift), R(T) is the sensor coil resistance at temperature T and R(80) is the sensor coil resistance at 80° C. Based on these results, the total resistance drift was approximately 13% over the entire temperature range. As shown in FIG. 3A, the plot shows a linear relationship (linear curve) between resistance drift and temperature and the slope $b_0$ for this resistance change is relatively constant at approximately 0.30%/degree for all of the sensors 10 tested. Accordingly, a resistance drift factor $b_0$, e.g. 0.30 (slope of the resistance versus temperature data), is predetermined, set and stored in the signal processor 48 for the location system 30.

Additionally, sensitivity (S) in V/gauss at KHz was also measured for each of the sensors 10 over the temperature range and sensitivity drift $G_s$ was determined and plotted against temperature as shown in FIG. 3B. These sensitivity measurements S were converted to gradient values $G_s$ (as % drift of temperature sensitivity), i.e., the percentage difference of a sensor coil voltage at temperature T relative to its voltage at 80° C., according to the following equation:

$$Gs\ (\%) = \frac{|V(T) - V(80)|}{V(80)} \times 100$$

wherein $G_s$ is sensitivity drift as the gradient value in percent (% drift), V(T) is the coil voltage at temperature T and V(80) is the sensor coil voltage at 80° C. Based on these results, the total sensitivity drift is approximately 1.24% over the entire temperature range and the slope $a_0$ for this sensitivity drift versus temperature profile is approximately 0.025%/degree. Thus, a sensitivity drift factor $a_0$, e.g. the 0.25 slope, is a constant that is predetermined, set and stored in the signal processor 48 for the location system 30.

Temperature Sensitivity Algorithm and Use

Based on the testing conducted, a temperature sensitivity algorithm has been created for the location system 30. The data from the testing showed that the resistance change $b_0$ and the sensitivity change $a_0$ for the position sensors 10 tested are constants as evidenced by the results in Table (FIG. 6) and FIGS. 3A and 3B. Both of these constants ($a_0$ and $b_0$) are stored in the memory of the signal processor 48 for the location system 30.

Additionally, each position sensor 10 (used on the medical device 80) is calibrated at room temperature, for instance, temperature range between 20°–23° C. in order to set an initial sensitivity $S_0$ and an initial resistance $R_0$ for each position sensor 10. These values are also stored in the signal processor 48 in the memory portion, for instance, the EPROM.

When in use, the medical device 80 having the position sensor 10 is placed within a patient and within an externally applied generated AC magnetic field from a plurality of magnetic field generators (not shown) positioned external to the patient. When using the medical device 80, for instance in a procedure such as an ablation procedure, current (I) is delivered through the position sensor 10 as a consistent and uniform signal, for instance, a 4 KHz signal delivered by the location system 30. The voltage value is determined at the sensor 10 and the voltage value is converted to the resistance value R(T) by signal processor 48 according to the formula R(T)=V/I. In turn, the real time temperature (T) at the position sensor 10 is determined according to the formula:

$$T = \frac{R(T) - R_o}{b_0}$$

where R(T) is the resistance determined at the current or real time temperature at the position sensor 10, $R_0$ is the initial resistance determined during the calibration procedure and recalled from the signal processor memory and $b_0$ is the resistance drift factor also recalled from memory.

The next step after calculating the real time temperature T is to determine the current or real time sensitivity S(T) of the position sensor 10 at this temperature according to the formula:

$$S(T) = S_0 + a_0 \times T$$

where $S_0$ is the initial sensitivity for the position sensor 10, $a_0$ is the sensitivity drift factor (both determined during the calibration procedure and recalled from memory), and T is the real time temperature calculated above.

In the next step, the position and orientation algorithm (location algorithm) of the location system 30 is adjusted in order to account for the real time sensitivity S(T) which is now used as a correction factor for the position and orientation algorithm according to the formula:

$$B = \frac{V}{S(T)}$$

where B is the calculated magnetic field at the measured at the position sensor 10, V is the voltage at the position sensor 10 and S(T) is the real time sensitivity of the position sensor 10 at the real time temperature. In turn, the new magnetic field measurement B is used in the position and orientation algorithm to calculate the location, e.g. the position and orientation, of the position sensor 10.

Accordingly, at any given moment during use of the medical device 80 and the location system 30, the accuracy of the position and orientation coordinate information derived from the position sensor 10 is maintained to an accuracy of $\leq 1$ mm and preferably $\leq 0.5$ mm through use of the temperature sensitivity algorithm in accordance with present invention.

Accuracy Testing

Additionally, another test was performed to measure the effect of sensor coil core composition on the determined location of a medical device 80 under simulated ablation conditions (high temperature) using the apparatus, including the location system 30, schematically shown in FIG. 4. The distal tips of medical devices, e.g. an ablation catheter 80 and a reference catheter 80a were securely fastened in water bath 44 to prevent movement of the catheter tips during the test. The ablation catheter 80 and reference catheter 80a both contained position sensors. In addition, the ablation catheter 80 was equipped with a 4 mm long ablation electrode 91 at its distal tip. The bath was filled with salt water having an impedance of about 100 ohms to simulate blood. The proximal ends of the catheters 80 and 80a were connected to junction box 46 through which electrical signals from and to the position sensors and electrode 91 could be received and transmitted. Junction box 46 was connected to signal processor 48 to compute the location (in position and orientation coordinate form) of the ablation catheter tip 80 relative to the reference catheter tip 80a. RF generator 50 was connected to junction box 46 to supply RF energy to the ablation electrode 91 at the distal tip of ablation catheter 80. RF generator return electrode 52 was also contained in bath 44 and was connected to RF generator 50.

The apparatus of FIG. 4 was contained within a magnetic field generated by three magnetic field generator elements, e.g. electromagnets (not shown) arranged in a triangular arrangement roughly 40 cm between centers positioned below the apparatus. For each catheter tested, ten location readings were made prior to supplying RF energy to the catheter tip electrode 91. Another ten location readings were made after the supply of RF energy was initiated to the distal tip electrode at a power level of 70 W. Several types of catheters were evaluated. The catheter types included catheters having location sensors having sensor coil cores comprising ferrite; catheters having location sensors with sensor coil cores comprising carbonyl iron and in accordance with the present invention, catheters 80 having sensor coils 10 with cores 12 made of Wiegand effect material. The temperature sensitivity correction algorithm was employed by the signal processor 48 when testing the catheters 80 having the sensor coils 10 with Wiegand effect material cores 12 of the present invetion.

Since the catheter tips were securely fastened to the bath during the tests, absent any location error, the catheter tips should have registered the same location before and during the supply of RF energy to the distal tip electrodes. In fact, differences between tip location before and during supply of RF energy were observed. The average location error of the catheters during simulated ablation conditions (defined as the absolute value of the difference in tip location before and during supply of RF energy to the catheter tip electrode) as a function of sensor core composition is shown in Table 2 below.

TABLE 2

LOCATION ERROR (MM) AND SENSITIVITY (V/GAUSS AT 3 KHZ) AS A FUNCTION OF SENSOR COIL CORE COMPOSITION

| SENSOR COIL CORE COMPOSITION | AVERAGE LOCATION ERROR (mm) | SENSITIVITY (V/GAUSS) |
| --- | --- | --- |
| Ferrite | 5.9 | 3.0 |
| Carbonyl Iron | 0.4 | 3.3 |
| Wiegand Alloy | 0.5 | 7.0–8.0 |

As shown in Table 2, although the sensor coil 10 with the Wiegand effect material (Wiegand alloy) core 12 demonstrated a greater than 2× increase in sensitivity over both the ferrite and carbonyl iron core sensor coils, a high degree of accuracy was still maintained, e.g. only 0.5 mm error. This minimal error in the position and orientation coordinate information was a direct result of the temperature sensitivity correction algorithm according to the present invention. Accordingly, even though the position sensor 10 according to the present invention reflected an overall sensitivity ranging from between 7.0–8.0 V/gauss, the position sensor 10 demonstrated a high degree of accuracy due to its minimal location error. Thus, the position sensor 10 according to the present invention is particularly useful for various medical applications including even those medical applications that experience high temperatures up to 80° C. such as thermal ablation procedures. Moreover, the average location error of approximately 0.5 mm for the position sensor 10 of the present invention and this is extremely close, if not negligible, to the location error observed with the carbonyl iron core sensor coils even though these coils demonstrate lower sensitivity. Thus, there is a negligible drop-off in accuracy in exchange for the significant decrease in size afforded by the position sensor 10 of the present invention. A size benefit that cannot be achieved with position sensors utilizing either ferrite or carbonyl iron as its core material because of challenges posed by the handling and manufacturing requirements of these two materials. The drawbacks associated with these two materials are due to characteristics such as brittleness in these materials which have an overall limitation on the ratio between length and diameter for the sensor. Accordingly, since the position sensor 10 of the present invention eliminates these drawbacks, it can be utilized in much smaller sized devices, such as sizes outlined above, than previuosly thought possible.

Temperature Measurement with Position Sensor

The present invention also includes a method for measuring the temperature adjacent the position sensor (sensor coil) 10 on the medical device 80 utilizing the sensor coil 10 and the position and orientation system 30. The method of measuring temperature, at the medical device 80, in accordance with the present invention includes establishing a temperature measurement signal distinct from the signal used to energize the electromagnetic field generators (not shown) of the system 30. As with the field generator signal, the temperature measurement signal is an AC signal. However, the temperature measurement signal is at a different frequency from the frequency used to drive the field generators.

The temperature measurement signal is a uniform AC signal transmitted to the sensor coil 10 by the system 30. For instance, the field generators are driven by a field generator signal having a frequency of 3 KHz and the temperature measurement signal sent to the sensor coil 10 has a frequency of 4 KHz.

As the medical device 80 is used in a medical procedure, for instance an ablation procedure, the temperature generated during the procedure by the device 80 or other devices which may be utilized along with the device 80 are monitored and measured by the system 30 using the sensor coil 10 of the device 80. As mentioned above, the method according to the present invention is particularly useful for direct measurement of temperatures adjacent the sensor coil 10 of the device 80.

In measuring temperature, the temperature measurement signal, for instance a 4 KHz signal, is provided to the sensor coil 10 and the voltage across the sensor coil 10 is measured by the system 30 through the signal processor 48. Since the temperature measurement signal, e.g. current (I) and the measured voltage are both known at this point, the signal processor 48 readily determines the resistance at the sensor coil 10 based on these two values.

In accordance with the temperature sensitivity algorithm of the present invention outlined above, the resistance value determined by the signal processor 48 (based on the temperature measurement signal and the measured voltage) is adjusted by the resistance drift factor $b_0$ constant) by the signal processor 48. Accordingly, this adjustment allows the signal processor 48 to accurately determine the actual temperature at the sensor coil 10.

Accordingly, in a temperature measurement method in accordance with the present invention, the medical device 80 having sensor coil 10 is placed within a patient and within a magnetic field at a desired site for performing a medical procedure with the device 80. The position and orientation system 30 generates a magnetic field through a generator signal provided to the plurality of magnetic field generators (not shown). As mentioned above, a field generator signal at a first frequency, for instance 3 KHz is provided to the field generators and a temperature measurement signal (I) at a second frequency, for instance 4 KHz, is provided to the sensor coil 10.

As the medical device 80 is being used at the desired site within the patient and within the externally applied magnetic field, a voltage measurement is made by the signal processor 48 in order to measure the voltage across the sensor coil 10. In accordance with the algorithm described above, both the temperature measurement signal (I) and the measured voltage value are used by the signal processor 48 to determine a resistance value at the sensor coil 10. And, in accordance with this algorithm, an actual temperature value is determined in real time based on the actual temperature measured with the sensor coil 10.

Thus, with the actual temperature value, the operator or physician utilizing the system 30 can take appropriate actions. For instance, if the temperature generated during a procedure, such as an ablation procedure, becomes too high, for instance, exceeds 80° C., the physician may want to pause the procedure and allow for the temperature to cool at the site prior to continuing with the procedure. This is a direct safety benefit to the patient.

Accordingly, the temperature measurement method according to the present invention provides the physician with great flexibility and avoids having to use separate temperature monitors or temperature sensors such as thermocouples. Thus, by utilizing the sensor coil 10 in accordance with the present invention, the overall costs of the medical procedure are also reduced.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A medical location system comprising:
   a medical device having a body;
   a position sensor at a portion of the body, the position sensor having a core made of a Wiegand effect material; and a winding circumferentially positioned around the core, the position sensor providing signals that are used to determine temperature at the position sensor and are used to determine location information of the portion of the body of the medical device; and
   a signal processor having a temperature sensitivity algorithm and a location algorithm and, which is coupled to receive the signals from the position sensor, the signal processor determining a temperature at the position sensor using the temperature sensitivity algorithm and location information of the portion of the body of the medical device based on the signals received from the position sensor using the location algorithm.

2. The medical location system according to claim 1, wherein the location information comprises position coordinates.

3. The medical location system according to claim 2, wherein the location information further comprises orientation coordinates.

4. The medical location system according to claim 3, wherein the position sensor has an accuracy within approximately 0.5 mm.

5. The medical location system according to claim 1, wherein the signal processor determines the location information with accuracy of $\leq 1$ mm at temperatures greater than 75° C.

6. The medical location system according to claim 5, wherein the signal processor determines the location information with accuracy of $\leq 1$ mm at temperatures at approximately 80° C.

7. The medical location system according to claim 1, wherein the core has an outer diameter less than approximately 0.3 mm.

8. The medical location system according to claim 7, wherein the core has an outer diameter of about 0.25 mm.

9. The medical location system according to claim 8, wherein the winding is attached to the core.

10. The medical location system according to claim 9, wherein a combination of the core and the wire winding has an outer diameter less than approximately 0.5 mm.

11. The medical location system according to claim 10, wherein the combination of the core and the winding have an outer diameter of about 0.4 mm.

12. The medical location system according to claim 11, wherein the material of the core comprises cobalt.

13. The medical location system according to claim 12, wherein the material of the core further comprises vanadium.

14. The medical location system according to claim 13, wherein the material of the core further comprises iron.

15. The medical location system according to claim 14, wherein the material of the core comprises approximately 20%–80% cobalt.

16. The medical location system according to claim 14, wherein the material of the core comprises approximately 2%–20% vanadium.

17. The medical location system according to claim 14, wherein the material of the core comprises approximately 25%–50% iron.

18. The medical location system-according to claim 14, wherein the material of the core comprises approximately 52% cobalt, 10% vanadium and 38% iron.

19. The medical location system according to claim 9, wherein the winding is made of copper.

20. The medical location system according to claim 1, wherein the signal processor senses a variation in an electrical characteristic of the winding, and determines the temperature of the position sensor responsively to the variation.

21. The medical location system according to claim 20, wherein the electrical characteristic comprises a resistance.

22. A medical location system comprising:
a medical device having a body;
a position sensor at a portion of the body, the position sensor having a core made of a high permeable material, the material being a bi-stable magnetic material that produces a substantially uniform voltage pulse upon an application of an external field, the position sensor providing signals that are used to determine location information of the portion of the body and are used to determine temperature at the position sensor; and
a signal processor having a temperature sensitivity algorithm and a location algorithm and, which is coupled to receive the signals from the position sensor, the signal processor determining a temperature at the position sensor using the temperature sensitivity algorithm and location information of the portion of the body of the medical device based on the signals received from the position sensor using the location algorithm.

23. The medical location system according to claim 22, further comprising a winding circumferentially positioned around the core.

24. The medical location system according to claim 22, wherein the location information comprises position coordinates.

25. The medical location system according to claim 24, wherein the location information further comprises orientation coordinates.

26. The medical location system according to claim 25, wherein the position sensor has an accuracy within approximately 0.5 mm.

27. The medical location system according to claim 22, wherein the signal processor determines the location information with accuracy of $\leq 1$ mm at temperatures greater than 75° C.

28. The medical location system according to claim 27, wherein the signal processor determines the location information with accuracy of $\leq 1$ mm at temperatures at approximately 80° C.

29. The medical location system according to claim 22, wherein the core has an outer diameter less than approximately 0.3 mm.

30. The medical location system according to claim 29, wherein the core has an outer diameter of about 0.25 mm.

31. The medical location system according to claim 30, wherein the position sensor comprises a winding, wherein the winding is attached to the core.

32. The medical location system according to claim 31, wherein a combination of the core and the winding has an outer diameter less than approximately 0.5 mm.

33. The medical location system according to claim 32, wherein the combination of the core and the winding have an outer diameter of about 0.4 mm.

34. The medical location system according to claim 33, wherein the material of the core comprises cobalt.

35. The medical location system according to claim 34, wherein the material of the core further comprises vanadium.

36. The medical location system according to claim 35, wherein the material of the core further comprises iron.

37. The medical location system according to claim 36, wherein the material of the core comprises approximately 20%–80% cobalt.

38. The medical location system according to claim 36, wherein the material of the core comprises approximately 2%–20% vanadium.

39. The medical location system according to claim 36, wherein the material of the core comprises approximately 25%–50% iron.

40. The medical location system according to claim 36, wherein the material of the core comprises approximately 52% cobalt, 10% vanadium and 38% iron.

41. The medical location system according to claim 31, wherein the winding is made of copper.

42. The medical location system according to claim 22, wherein the material of the core comprises a copper, nickel and iron alloy (CuNiFe).

43. The medical location system according to claim 22, wherein the material of the core comprises an iron, chrome and cobalt alloy.

44. The medical location system according to claim 22, wherein the signal processor senses a variation in an electrical characteristic of the position sensor, and determines the temperature of the position sensor responsively to the variation.

* * * * *